United States Patent
Lin et al.

(10) Patent No.: US 9,170,240 B2
(45) Date of Patent: Oct. 27, 2015

(54) ULTRASONIC PARTICLE MEASURING SYSTEM

(75) Inventors: Yaoying Lin, Freising (DE); Beat Kissling, Reinach (CH); Wolfgang Drahm, Erding (DE); Thomas Frohlich, Munchenstein (CH)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 374 days.

(21) Appl. No.: 13/808,649

(22) PCT Filed: Jun. 20, 2011

(86) PCT No.: PCT/EP2011/060192
§ 371 (c)(1),
(2), (4) Date: Jan. 7, 2013

(87) PCT Pub. No.: WO2012/004114
PCT Pub. Date: Jan. 12, 2012

(65) Prior Publication Data
US 2013/0104657 A1    May 2, 2013

(30) Foreign Application Priority Data
Jul. 8, 2010   (DE) .......................... 10 2010 031 129

(51) Int. Cl.
*G01N 29/02* (2006.01)
*G01N 29/44* (2006.01)
(Continued)

(52) U.S. Cl.
CPC ................ *G01N 29/44* (2013.01); *G01N 15/02* (2013.01); *G01N 15/06* (2013.01); *G01N 29/02* (2013.01);
(Continued)

(58) Field of Classification Search
CPC ....... G01N 15/02; G01N 29/02; G01N 29/44; G01N 29/48; G01N 2291/02408; G01N 15/06; G01N 29/2291; G01N 29/348; G01N 29/2456
USPC .......................... 73/602, 61.45, 646; 702/190
See application file for complete search history.

(56) References Cited

U.S. PATENT DOCUMENTS

| 3,779,070 A | 12/1973 | Cushman |
| 4,706,509 A | 11/1987 | Riebel |

(Continued)

FOREIGN PATENT DOCUMENTS

| DE | 2257802 | 6/1973 |
| WO | 9919723 A1 | 4/1999 |
| WO | 2011/051006 A1 | 5/2011 |

OTHER PUBLICATIONS

International Search Report, EPO, The Netherlands, Aug. 18, 2011.
(Continued)

*Primary Examiner* — J M Saint Surin
(74) *Attorney, Agent, or Firm* — Bacon & Thomas, PLLC

(57) ABSTRACT

An ultrasonic particle measuring system having an ultrasonic transducer with at least one ultrasonic transducer element and at least one coupling element, wherein, during operation, acoustic signals are transmittable and receivable by the ultrasonic transducer element via the coupling element, wherein the coupling element is embodied as an acoustic lens, and the ultrasonic, particle measuring system has an evaluation unit suitable for amplitude analysis of reflection signals of acoustic signals reflected from particles to the ultrasonic transducer, and wherein, with the evaluation unit, amplitudes of reflection signals in a predetermined time interval are countable, which are greater than a predetermined threshold value.

14 Claims, 2 Drawing Sheets

(51) Int. Cl.
    *G01N 15/02*     (2006.01)
    *G01N 15/06*     (2006.01)
    *G01N 29/22*     (2006.01)
    *G01N 29/24*     (2006.01)
    *G01N 29/34*     (2006.01)
    *G01N 29/48*     (2006.01)

(52) U.S. Cl.
    CPC .......... *G01N 29/221* (2013.01); *G01N 29/2456* (2013.01); *G01N 29/348* (2013.01); *G01N 29/48* (2013.01); *G01N 2291/02408* (2013.01); *G01N 2291/02416* (2013.01)

(56) References Cited

U.S. PATENT DOCUMENTS

| | | | |
|---|---|---|---|
| 5,121,629 A | 6/1992 | Alba | |
| 6,205,848 B1 | 3/2001 | Faber et al. | |
| 6,481,268 B1 | 11/2002 | Povey et al. | |
| 6,736,010 B1 | 5/2004 | Muller et al. | |
| 7,114,375 B2 | 10/2006 | Panetta | |
| 7,360,403 B2* | 4/2008 | Jones et al. | 73/61.75 |
| 7,484,414 B2* | 2/2009 | Priev et al. | 73/649 |
| 7,673,526 B2* | 3/2010 | Bailey et al. | 73/861.27 |
| 7,719,170 B1* | 5/2010 | Kim et al. | 310/335 |
| 8,490,498 B2* | 7/2013 | Wiest et al. | 73/861.28 |
| 2008/0194967 A1* | 8/2008 | Sliwa et al. | 600/472 |
| 2009/0122639 A1* | 5/2009 | Hall et al. | 367/7 |
| 2010/0087735 A1* | 4/2010 | Hall et al. | 600/437 |

OTHER PUBLICATIONS

German Search Report, the German PTO, Munich, Feb. 10, 2011.

International Preliminary Report on Patentability dated Jan. 8, 2013, issued in Geneva, Switzerland, in International Application No. PCT/EP2011/060192.

* cited by examiner

ULTRASONIC PARTICLE MEASURING SYSTEM

TECHNICAL FIELD

The present invention relates to an ultrasonic, particle measuring system, including an ultrasonic transducer, which has at least one ultrasonic transducer element and at least one coupling element, wherein, during operation, acoustic signals are transmittable and receivable by the ultrasonic transducer element via the coupling element, and wherein the ultrasonic transducer is arranged in a measuring tube.

BACKGROUND DISCUSSION

Ultrasonic transducers are composed, normally, of an electromechanical transducer element, e.g. a piezoelectric element, also called a piezo for short, and a coupling layer, also called a coupling wedge or, not so frequently, a lead-in element. The coupling layer is, in such case, most often manufactured of synthetic material, while the piezoelectric element is composed in industrial process measurement technology usually of a piezoceramic. The ultrasonic waves are produced in the piezoelectric element and led via the coupling layer to the tube wall and from there into the liquid.

Arranged between the piezoelectric element and the coupling layer can be another coupling layer, a so called adapting, or matching, layer. The adapting, or matching, layer, in such case, performs the function of transmission of the ultrasonic signal and simultaneously the reduction of a reflection at interfaces between two materials caused by different acoustic impedances.

Known are also ultrasonic methods and measuring devices for ascertaining concentration and/or size of particles in a fluid as measured medium. Thus, U.S. Pat. No. 6,481,268 shows such a measuring device having at least one ultrasonic transducer. The ultrasonic signal transmitted by the ultrasonic transducer is reflected by particles in the measured medium back to the transducer and there registered as an echo. One embodiment shows two ultrasonic transducers arranged opposite one another on a measuring tube. These transmit and/or receive the ultrasonic signals essentially perpendicularly to the measuring tube axis. Another embodiment shows an individual ultrasonic transducer with a coupling element, which is embodied as a lens, in order to focus the ultrasonic signal into the measuring tube. A measuring of flow is not provided in this document.

In an additional patent of the state of the art, U.S. Pat. No. 5,251,490, an ultrasonic flow measuring device is shown, which ascertains flow through a measuring tube with the Doppler measuring principle. Ultrasonic signals are transmitted in the form of waves, focused by an acoustic lens and reflected on particles in the measured medium. The reflections are greatest in the direct vicinity of the focus. The flow velocity of the liquid is determined from the frequency shift between the in-coupled and reflected waves.

U.S. Pat. No. 5,533,408 discloses an ultrasonic flow measuring device using a combination of the travel-time difference principle and the Doppler principle. In this regard, however, each case has its own sensor. Switching between the sensors of the two measuring principles happens upon the exceeding, or subceeding, of a predetermined measured value.

WO 03/102512 A1 proposes a method for travel-time difference measurement of a flowing fluid, wherein, supplementally, the reflections of the ultrasonic signal on particles in the fluid are ascertained, in order to learn therefrom the concentration of the particles. In this regard, two ultrasonic transducers are usually provided for a travel-time difference measurement, wherein at least one of these ultrasonic transducers is switchable so rapidly from a transmitting state to a receiving state that it can receive the reflections of its transmitted signal on the particles in the fluid, or additional ultrasonic transducers are provided, which are so arranged that they can receive the reflections. For ascertaining the concentration and the size of the particles in the measured medium, the Doppler shift of the moving particles is evaluated. Measurement in motionless measured medium is, thus, not possible.

SUMMARY OF THE INVENTION

An object of the invention is to provide a simple ultrasonic, particle measuring system, with which particle count per unit time and/or particle size of particles in a measured medium are ascertainable from a predetermined order of magnitude.

The object is achieved by an ultrasonic, particle measuring system which includes at least one ultrasonic transducer element and at least one coupling element, wherein, during operation, acoustic signals are transmittable and receivable by the ultrasonic transducer element via the coupling element. The ultrasonic transducer element is e.g. so arranged in a measuring tube that the acoustic signals propagate along at least one signal path in the measuring tube, for example, at an angle of 90° to the measuring tube axis or even at a smaller angle. The coupling element is, in such case, embodied as an acoustic lens. Furthermore, the ultrasonic, particle measuring system includes an evaluation unit suitable for amplitude analysis of reflection signals of the acoustic signals reflected from the particles to the ultrasonic transducer, wherein, with the evaluation unit, magnitudes of the amplitudes of the reflection signals received by the ultrasonic transducer are ascertainable and wherein, with the evaluation unit, the number of amplitudes greater than a predetermined threshold value in a predetermined time interval are countable.

The evaluation unit is suitable for registering and for evaluation of amplitudes of signals of the acoustic reflection signals received by the ultrasonic transducer element, which are reflection signals of particles in the measured medium reflected back to the ultrasonic transducer from acoustic signals transmitted by the ultrasonic transducer. The evaluation unit thus analyzes amplitudes of these reflection signals received by the ultrasonic transducer, wherein at least those magnitudes are ascertainable, which are greater than a predetermined threshold value, and wherein at least their number in a predetermined time interval are countable. From the amplitudes of the received reflection signals, which are greater than a predetermined threshold value, the particle sizes of the particle in the measured medium are ascertained. This occurs via an associating of amplitude magnitudes with particle sizes. Thus, only particles of a predetermined size are ascertainable. There is both a minimum size, as well as also a maximum size of particle. If there are particles greater than the maximum size, these can no longer be differentiated in their size. The maximum size results essentially from the focusing of the lens. From the number of amplitudes, which are greater than a predetermined threshold value, in the reflection signals received in a predetermined time interval, the particle concentration of particles of a predetermined minimum size in the measured medium is ascertained.

The coupling element is embodied as an acoustic lens, for example, as a planoconcave acoustic lens or as an acoustic Fresnel lens. The coupling element includes a first contact surface, which, during operation, contacts the measured medium, and at least one other, second contact surface, on which the ultrasonic transducer element is arranged and secured. The first contact surface has, for example, a contour with an acoustically effective radius of curvature greater than 5 mm. Especially, this acoustically effective radius of curvature is greater than 10 mm. In an embodiment, the acoustically effective radius of curvature amounts to, at most, 150 mm, especially, at most, 50 mm. The radius of curvature is dependent on the measuring tube diameter and on the material of the coupling element as well as the chemical composition and the physical properties of the measured medium, since especially the propagation velocity of the acoustic signal depends on the material, in which the acoustic signal propagates.

Lenses are, conventionally, bordered by at least one ellipsoidal or spherical surface. A sphere has overall the same curvature, so that such lenses are definable via the curvature. Somewhat the same is true for an ellipsoid. A exception is formed by, for example, Fresnel lenses. Fresnel lenses are divided into a number of, for example, annular sections, which in cross section can be approximated by prisms. Ideally, the annular sections of a Fresnel lens form a section of a conventional lens with a predetermined radius of curvature. This is then advantageously equal to the acoustically effective radius of curvature.

Naturally, the acoustically effective radius of curvature and the focal lengths of a lens are combined with one another via the refractive characteristics. These depend, in turn, on the velocities of sound in the measured medium, respectively in the coupling element.

An advantage of a Fresnel lens can be the low thickness of the lens in comparison to conventional lenses. In this way, the coupling element can be embodied to be very thin, whereby it can act as an adapting, or matching, layer between measured medium and ultrasonic transducer element by matching the impedances of the two contact partners with one another. Another advantage results from a special embodiment of the Fresnel lens. It has individual steps with a respective height, which are, in each case, approximately $n*\lambda/2$, with n being a natural number and $\lambda$ the wavelength of the acoustic signal in the lens. The lens is thus virtually executed as a $\lambda/2$ adapting, or matching, layer, which leads to an improved transmission of the acoustic signal in comparison to a conventional lens.

The ultrasonic transducer can be secured in the measuring tube, wherein the coupling element of the ultrasonic transducer then contacts the measured medium during operation, especially with its first contact surface. This is, thus, a so called inline-ultrasonic, particle measuring system.

An ultrasonic, particle measuring system of the invention is thus used, especially, in a plant of the process industry, especially in a pipeline system after a particle filter, for monitoring the functioning of the filter, e.g. for diagnosis of whether e.g. small leaks are present or how great the permeability of the filter is for particle from a certain size, e.g. from a diameter of 1 μm. The diameter of the particles is deduced based on a model. Actually, the reflecting area is decisive for the reflection signal. However, the particles in the model are assumed to be spheres. In such case, the particles are not greater than 100 μm, especially, they have a diameter not greater than 10 μm, and the measured medium is not more turbid than 100FNU, or the turbidity of the measured medium is e.g. less than 10FNU. In the case of a very turbid measurement signal, the acoustic signal would possibly be absorbed, and a flow measurement is then no longer possible. Therefore, only media should be measured, which still appear clear to the human eye. Here, no highly accurate turbidity measurement is required. the present ultrasonic, particle measuring system can first deliver an indication of a malfunction, when it is embodied according to the invention. A further method of the invention is the retrofitting of an already existing ultrasonic flow measuring system with at least one coupling element of the invention embodied as a lens. An option, in such case, is to replace a complete ultrasonic transducer without lens with an ultrasonic transducer of the invention, or the coupling element is replaced. In additional embodiments of the invention, the height of the predetermined threshold value during operation is adaptable and/or, in the case of exceeding the predetermined threshold value, an alarm is issuable.

In contrast to turbidity measuring systems, with an ultrasonic, particle measuring system of the invention, it is not the turbidity of the measured medium that is ascertained according to one of the standards for turbidity measurement, but, instead, only, as already described, the frequency of particles occurring in the measured medium, from a certain size. It involves, thus, more a particle counter than a turbidity measuring device. Since the amplitudes of the reflections on the particles are evaluated for the particle measurement, without having to calculate a Doppler shift, the particles are also theoretically measurable in the case of very slowly flowing media, even in the case of standing media.

By the focusing by means of the acoustic lens, the particles are determined only in a small volume of the flow of the measured medium in the measuring tube. This volume depends on the acoustically effective radius of curvature ROC of the lens, the velocities of sound in the lens $c_{Lens}$ and in the measured medium $c_{Medium}$ and the wavelength of the acoustic signal $\lambda_{Medium}$. The volume can, in such case, be assumed, e.g. as cylindrical and is then referred to as a focal tube. The radius of this focal tube around the focal point can be expressed, for example, as $$r_0 = 0.257 \frac{\lambda f'}{a},$$

wherein a stands for the radius of the ultrasonic transducer element and $$f' \approx \frac{ROC}{1 - \frac{c_{lens}}{c_{medium}}}.$$

The length of the focal tube amounts then e.g. to $$l_f \approx 1.8 \lambda \left(\frac{f'}{a}\right)^2.$$

With an ROC of 5 mm, a length of the focal tube of 0.5 mm and a radius of the focal tube of 0.26 mm, there results a volume 0.11 mm³. Assuming that the ROC amounts to 50 mm, length and radius are 50.1 mm and 2.6 mm, respectively, the volume becomes 1064 mm³. In these Examples, the ultrasonic transducer element is assumed to be circular. The radius of the ultrasonic transducer element, for example, a piezoelectric element, naturally limits the acoustic signal transversely to its propagation direction in the instant of the transmission. It is in this volume that the acoustic signals are reflected on the particles, this meaning thus that it could also be referred to as the measurement volume. A very large part of the energy of the acoustic signal is concentrated in this volume. Particles can only be measured, when the acoustic signals are sufficiently reflected on them. This is, for example, the case for most solid particles. Playing a great role for the reflection are, besides the angle of incidence of the acoustic signal on the surface of a particle, also the acoustic impedance of particles and measured medium, and the velocities of sound in their materials. If measured medium and particles have identical acoustic impedances, then there is no reflection. The acoustic impedances must thus lie sufficiently apart, that sufficient reflections result. With a lifting or sinking of the threshold value, from which the amplitudes of the reflection signals are clearly picked up, it is, thus, possible also to adjust, which type of particles are to be taken into consideration.

The ultrasonic, particle measuring system includes a control unit, which is suitable for exciting the ultrasonic transducer element for transmitting at least two acoustic signals of different frequency. These are radiated especially approximately perpendicularly from the ultrasonic transducer element. If the ultrasonic transducer element has thus e.g. a disk-shaped form, the acoustic signals are normal. If the disk-shaped ultrasonic transducer element is then arranged parallel to a measuring tube axis, the acoustic signals are transmitted perpendicularly to the measuring tube axis from the ultrasonic transducer element.

The frequency range of the transmitted acoustic signals is, in such case, variably adjustable, for example, between a lower and an upper limit value. Usually, only one frequency, hereinafter called the 'measuring frequency', is used for the described measuring of the particles. This is, however, variable, between a first and at least one additional, second frequency. Especially, the measuring frequency, and, therewith, the first frequency and the second frequency, lie in a range from 2 MHz to 10 MHz. The resolution of the ultrasonic particle measurement system rises with the measuring frequency of the acoustic signals used for measuring. Smaller particle are detected with higher frequencies. Therefore, an embodiment of the invention includes a variable threshold value. This is predetermined as a function of the application of the ultrasonic particle measurement system, for example, set by the user, or it is predetermined as a function of the measured medium. It can also be predetermined by the ultrasonic, particle measuring system, e.g. as a function of the amplitudes of the reflection signals of the acoustic signals reflected from the particles in the measured medium to the ultrasonic transducer. Especially, the threshold value is predetermined as a function of the frequency of the acoustic signals produced by the ultrasonic transducer.

The measuring frequency is, for example, adjustable by the user. The user makes the frequency settings depending on the application. Alternatively, the ultrasonic, particle measuring system undertakes the adjusting of the measuring frequency, for example, by, from time to time, utilizing all frequencies of a predetermined frequency range for measuring and selecting the measuring frequency according to a predetermined specification, until the next point in time that the measuring frequency is reviewed.

In an embodiment, the ultrasonic, particle measuring system includes a control unit, e.g. a microprocessor, suitable for exciting the ultrasonic transducer element for transmitting an acoustic signal of a first form, especially a first burst-signal sequence, and suitable for exciting the ultrasonic transducer element for transmitting an acoustic signal of a second form, especially a second burst-signal sequence, which is different from the first form, especially the first burst-signal sequence is thus different from the second burst-signal sequence. Besides continuous signals, so-called continuous waves, burst-signals are applied for travel-time difference measurement by means of ultrasound, in this case, for particle detection. The differences in the signals can lie in the number of individual bursts in the burst-signal sequence and/or in the separations of the individual bursts in the burst-signal sequence and/or in the pulse shapes of the individual burst-signals. In the case of only a few bursts in a burst-signal sequence, the signal energy is smaller than in the case of many bursts. In order to obtain a sufficient amplitude of the reflection, correspondingly much signal energy must be transmitted into the measured medium. If, in contrast, very many bursts of rapid sequence are sent into the measured medium, there results thereby a narrow banded signal, similar to a narrow banded, continuous signal.

In a further development, the ultrasonic, particle measuring system is so embodied that the ratio of focal length the acoustic lens in aqueous measured media to a diameter of the measuring tube amounts to at least 0.2. In an embodiment of the solution of the invention, the ratio lies between 0.4 and 0.6. The ultrasonic transducer is placed in the measuring tube. In order not to influence the flow significantly, it protrudes, when at all, only to a small degree into the measuring tube. By the lens and its focusing, the acoustic signal is focused; there arises with this model a first signal cone. In signal propagation direction after the focusing, the acoustic signal is redispersed, it is wide. Thus, there arises with this model a second signal cone, which contacts with its tip the tip of the first signal cone at the focal point of the lens—there thus arises, in this model, a double cone.

With radius of curvature of the acoustic lens of the ultrasonic transducer from 5 mm to 50 mm and velocities of sound of about 2000 m/s to about 3000 m/s in the coupling element of the ultrasonic transducer embodied as an acoustic lens, focal lengths of 15 mm to 60 mm, in the case of measured media with velocities of sound in the measured medium of 1100 m/s to 1900 m/s.

Another further development of the invention provides that the coupling element is manufactured of a polymer, e.g. PEEK or PVC. Ultrasonic transducer elements are e.g. made of a piezoceramic or PVDF. In such case, according to an embodiment, the ultrasonic transducer element is adhered directly to a second contact surface of the coupling element. An adapting, or matching, layer usually arranged between coupling element and ultrasonic transducer element is omitted. A piezoceramic disk as ultrasonic transducer element or a PVDF disk or PVDF film is thus in direct contact with the coupling element, only with an adhesive layer therebetween. On the other hand, there are also liquid couplings, e.g. with fat or highly viscous oil, instead of the adhesive.

In an additional further development, at least the ultrasonic transducer element is excitable with a measuring frequency of at least 2 MHz. Most often, ultrasonic transducer elements are excited at a certain resonant frequency. They possess a relatively narrow usable frequency range. Therefore, also the receiving frequency lies usually in a region around the measuring frequency. An advantage of a high measuring frequency is the short wavelengths of the resulting acoustic signal, whereby the resolution in the particle measurement rises—small particles are registered, since also these reflect an echo back.

PVDF is more broadband than a piezoceramic. Furthermore, PVDF transducers have a better signal to noise ratio (SNR). However, the amplitudes are smaller in comparison with piezoceramic, which is disadvantageous especially for detection of smaller particles. The selection of the ultrasonic transducer element is correspondingly determined by the application of the ultrasonic, particle measuring system. If a broad usable frequency band is required, thus, application dependently, a large difference between the first and second frequencies, or an exact tunability to certain frequencies, PVDF is selected and applied as ultrasonic transducer element. If, in contrast, high amplitudes are needed, a piezoceramic is relied on as ultrasonic transducer.

In an additional further development of the ultrasonic, particle measuring system of the invention, it is provided that the measuring tube has an approximately circularly round cross section, with a diameter of at least 20 mm, especially at least 30 mm. At most, the measuring tube diameter amounts, for example, to 150 mm or e.g. even only 120 mm. The ultrasonic transducer, especially its lens, is correspondingly selected.

In the method of the invention for registering particles in the measured medium with an ultrasonic transducer of the invention, which is arranged in a measuring tube, wherein the acoustic signals propagate along at least one signal path in the measuring tube, the acoustic signals for registering particles in the measured medium are produced by the ultrasonic transducer by means of an amplitude analysis of reflection signals of the acoustic signals reflected from the particles to the ultrasonic transducer, thus the reflections of the acoustic signal on the particles. The acoustic signals produced by the ultrasonic transducer are focused according to the invention via an acoustic lens. The acoustic lens has, in such case, at least one focal point, which lies in a volume in the measuring tube. Acoustic signals propagate in the model along a straight signal path. Actually, their propagation is dependent on many factors and is e.g. lobe shaped.

In a further development of the method of the invention, from the amplitudes of the reflection signals received, which are greater than a predetermined threshold value, the particle sizes of the particle in the measured medium are ascertained, on which these reflection signals were reflected. The particle size is, thus, ascertained via the magnitude of the received amplitude of the reflection signal, i.e. the echo.

In an additional embodiment of the invention, for example, an alarm is output upon the exceeding of a predetermined threshold value and/or alarm is output upon the exceeding of a predetermined number of particles greater than a predetermined threshold value in a predetermined time interval.

In an additional embodiment of the invention, the level of the predetermined threshold value is adaptable during operation, e.g. by the user, or it is automatically adapted dependent on process parameters such as e.g. the measured medium and the particles located in the measured medium, especially their acoustic impedances in comparison to the acoustic impedance of the measured medium.

In an additional further development of the method of the invention, it is provided that, from the number of amplitudes of the reflection signals received in a predetermined time interval, thus from their frequency of occurrence, which amplitudes are greater than a predetermined threshold value, the particle concentration in the measured medium is ascertained. The ultrasonic transducer element delivers a voltage signal, which is processed in an evaluation unit. Naturally, the ultrasonic transducer element also registers disturbances, which are referred to as noise in the voltage signal. If, now, a threshold analysis of the signal is performed, only those values are further processed and, thus, recognized as particles, which lie above this predetermined threshold value. These amplitudes or peaks are, on the one hand, counted and therewith affect the particle frequency and, on the other hand, via their magnitude, the particle size is determined.

Another further development of the invention provides that the ultrasonic transducer is excited to a first burst-signal sequence and to a second burst-signal sequence, wherein the first burst-signal sequence is different from the second burst-signal sequence. Thus, two different burst-signal sequences can be used for the particle measurement.

In an additional further development of the method, at least the ultrasonic transducer is excited to a measuring frequency greater than 2 MHz. The measuring frequency can also be higher than 5 or 10 MHz, e.g. even 20 MHz. Since the wavelength of the acoustic signal is $\lambda=c/f$, with c the velocity of sound and f the measuring frequency, the wavelength smaller is in the case of a higher measuring frequency and otherwise same conditions. In this way, smaller particles are detectable. If the measuring frequency is much greater than 20 MHz, the absorption of the acoustic signal in the measured medium is very high, especially when only few particles are contained in the measured medium. A sufficiently strong acoustic signal for flow measurement is then only very difficulty implementable.

BRIEF DESCRIPTION OF THE DRAWINGS

The invention will now be explained in greater detail based on the appended drawing, whose figures contain different examples of embodiments. Equal elements are provided in the figures with equal reference characters. The figures of the drawing show as follows.

DETAILED DISCUSSION IN CONJUNCTION WITH THE DRAWINGS

Figure 1:
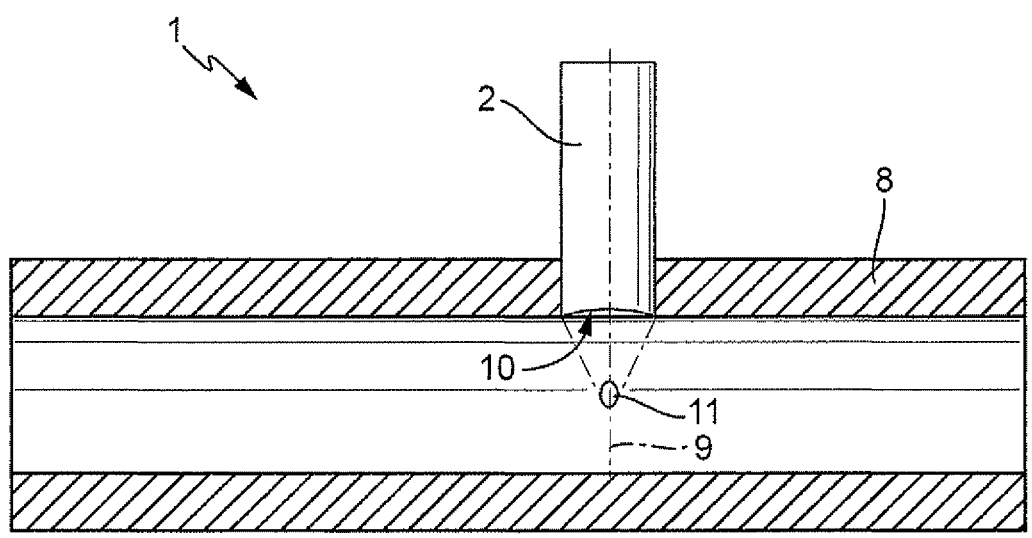
FIG. 1 is an ultrasonic, particle measuring system of the invention.

FIG. 1 shows, schematically, an ultrasonic, particle measuring system 1 of the invention. An ultrasonic transducer 2, which, via a coupling element, transmits and/or receives acoustic signals, is secured in a measuring tube 8 at an angle to the measuring tube axis. This is a so called inline measuring system. The central axis through the ultrasonic transducer 2 models here a signal path, along which ultrasonic signals propagate.

The ultrasonic transducer 2 includes an acoustic lens 10, which focuses ultrasonic signals in the measuring tube 8. The focal point of the acoustic lens 10 of the ultrasonic transducer 2 lies in the volume 11 for particle measurement. This volume 11 results from the focusing of the lens. It is here rotationally symmetric around the signal path 9 and drawn in the illustrated cross section essentially elliptically. In this volume, particles are registered by reflections of the acoustic signal on the particles.

An inventive use of the ultrasonic particle measurement system of the invention is e.g. in a pipeline system downstream from a filter, thus, in flow direction of the measured medium through the pipeline system, after the filter, e.g. for function monitoring of the filter.

Figure 2:
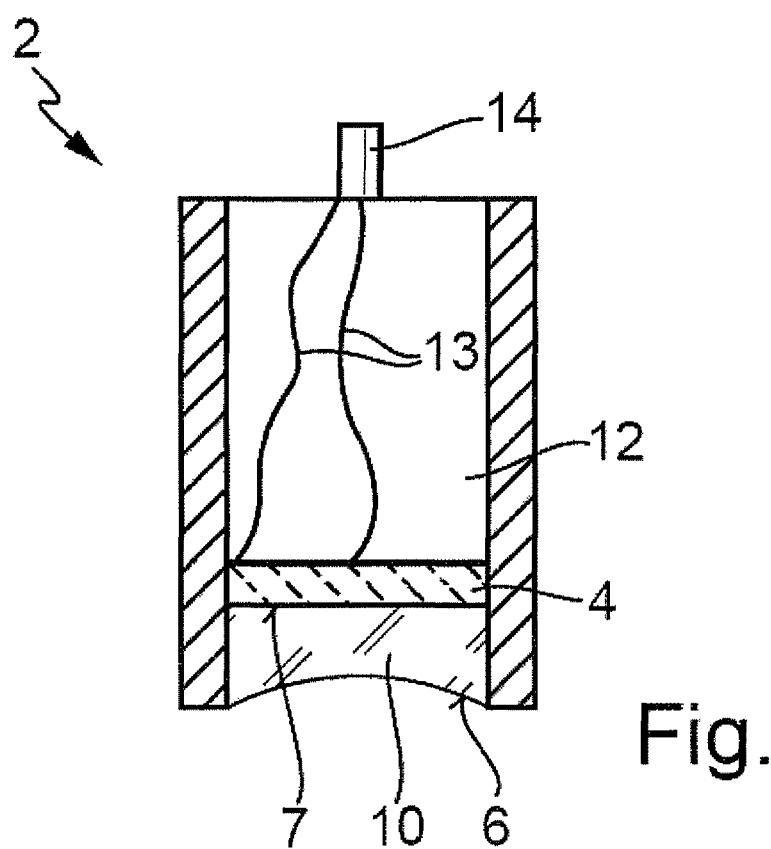
FIG. 2 is an ultrasonic transducer of an ultrasonic particle measurement system of the invention.

FIG. 2 illustrates the construction of an ultrasonic transducer 2 of the invention. This includes an ultrasonic transducer element 4, e.g. a high frequency-piezoceramic. Alternatively, also a PVDF disk is applicable as the ultrasonic transducer element. The ultrasonic transducer element 4 can both transduce electrical signals into mechanical oscillations and therewith into acoustic signals, as well as also acoustic signals into electrical signals. It functions, thus, both as sensor and as actuator. The ultrasonic transducer element 4 transmits and receives acoustic signals via a coupling element, which is embodied as an acoustic lens 10. The coupling element, respectively the acoustic lens, 10 has a plurality of surfaces, e.g. a first contact surface 6, which, during operation, contacts the measured medium in the measuring tube, and a second contact surface 7, which is in contact with the ultrasonic transducer element 4. The ultrasonic transducer element 4 is adhered, for example, directly on the second contact surface 7 of the acoustic lens 10, without any other adapting, or matching, layer therebetween. This should here, however, not be excluded.

The ultrasonic transducer element 4 is connected via two cables 13 and a plug connector 14 with a measurement transmitter (not shown). In the connector space 12 in the ultrasonic transducer 2 behind the ultrasonic transducer element 4, a so called backing can be provided, e.g. an oscillation damper, which is connected directly with the ultrasonic transducer element 4. The connector space 12 is bordered in this example by the housing 3 around the ultrasonic transducer element 4.

The lens 10 here is embodied as a planoconcave lens having a first contact surface 6, which has a predetermined radius of curvature, here e.g. 14 mm, and a planar, second contact surface 7. Equally, the lens 10 could be embodied as a Fresnel lens having a contoured first contact surface 6, which has an equally acoustically effective radius of curvature. A Fresnel lens is divided into a number of segments, or sections, which form together this contour with the acoustically effective radius of curvature.

The acoustically effective radius of curvature and the focal lengths of the lenses are related via the refractive indices, and these depend on the velocities of sound in the measured medium, respectively in the coupling element. The step height of a Fresnel lens is given, for example, by $n*\lambda/2$, wherein A is the wavelength of the acoustic signal in the coupling element and n a natural number.

The invention claimed is:

1. An ultrasonic particle measuring system, comprising:
   an ultrasonic transducer;
   which has at least one ultrasonic transducer element;
   at least one coupling element;
   a control unit; and
   an evaluation unit suitable for amplitude analysis of reflection signals of acoustic signals reflected from particles to said ultrasonic transducer, wherein:
   during operation, acoustic signals are transmittable and receivable by said ultrasonic transducer element via said coupling element;
   said coupling element is embodied as an acoustic lens;
   said ultrasonic, with said evaluation unit, amplitudes of reflection signals in a predetermined time interval are countable, which are greater than a predetermined threshold value;
   said ultrasonic transducer element is suitable for transmitting a first acoustic signal of a first frequency, and is suitable for transmitting a second acoustic signal of a second frequency;
   said control unit, is suitable for exciting said ultrasonic transducer element for transmitting the first acoustic signal and for exciting said ultrasonic transducer element for transmitting the second acoustic signal; and
   the first frequency is different from the second frequency;
   wherein particle sizes of the particles in the measured medium are ascertained from the amplitudes of reflection signals received, which are greater than a predetermined threshold value; and
   wherein particle concentration in the measured medium is ascertained from the number of amplitudes of reflection signals received in a predetermined time interval with amplitudes greater than the predetermined threshold value.

2. The ultrasonic particle measuring system as claimed in claim 1, wherein:
   the first frequency amounts to at least 2 MHz and the second frequency amounts to, at most, 10 MHz.

3. The ultrasonic particle measuring system as claimed in claim 2, wherein:
   the ultrasonic, particle measuring system is so embodied that the ratio of focal length of an acoustic lens in aqueous measured media to a diameter of said measuring tube amounts to at least 0.2.

4. The ultrasonic particle measuring system as claimed in claim 1, wherein:
   said ultrasonic transducer is arranged in a measuring tube for transmitting the first acoustic signal and the second acoustic signal along a shared signal path; and
   the shared signal path is so excited that it has an angle of 90° to said measuring tube axis.

5. The ultrasonic particle measuring system as claimed in claim 1, wherein:
   at least said coupling element is embodied as a planoconcave, acoustic lens.

6. The ultrasonic particle measuring system as claimed in claim 1, wherein:
   at least said coupling element is embodied as an acoustic, Fresnel lens.

7. The ultrasonic particle measuring system as claimed in claim 1, wherein:
   at least said coupling element is manufactured of a polymer.

8. The ultrasonic particle measuring system as claimed in claim 1, wherein:
   said ultrasonic transducer element is adhered directly to a second contact surface of said coupling element.

9. The ultrasonic particle measuring system as claimed in claim 1, wherein:
   the first frequency and the second frequency are adjustable.

10. The ultrasonic particle measuring system as claimed in claim 1, wherein:
    said measuring tube has an approximately circularly round cross section with a diameter of at least 20 mm.

11. The ultrasonic particle measurement system as claimed in claim 1, wherein
    the ultrasonic particle measuring system is arranged in a pipeline system downstream from a particle filter.

12. A method for registering particles in a measured medium with an ultrasonic transducer, which is arranged in a measuring tube, comprising the steps of:
    producing acoustic signals by the ultrasonic transducer for registering particles in the measured medium by means of amplitude analysis of reflection signals of the acoustic signals reflected from the particles to the ultrasonic transducer; and
    focusing at least the acoustic signals produced by the ultrasonic transducer via an acoustic lens, wherein:
    the frequency of the acoustic signals produced by the ultrasonic transducer is set within a predetermined frequency range according to a predetermined specification;
    wherein particle sizes of the particles in the measured medium are ascertained from the amplitudes of the reflection signals received, which are greater than a predetermined threshold value; and
    wherein particle concentration in the measured medium is ascertained from the number of amplitudes of reflection signals received in a predetermined time interval with amplitudes greater than the predetermined threshold value.

13. The method as claimed in claim 12, wherein:
the threshold value is predetermined as a function of the frequency of the acoustic signals produced by the ultrasonic transducer.
14. The method as claimed in claim 12, wherein:
the ultrasonic transducer is excited for transmitting the acoustic signal with a frequency greater than 2 MHz.

* * * * *